United States Patent [19]
Zadini et al.

[11] Patent Number: 5,978,714
[45] Date of Patent: Nov. 2, 1999

[54] EPICARDIAL PERCUTANEOUS DEVICE FOR ELECTRICAL CARDIAC THERAPY

[76] Inventors: Filiberto Zadini; Giorgio Zadini, both of 2237 Hilltop La., Camarillo, Calif. 93012

[21] Appl. No.: 08/871,658

[22] Filed: Jun. 6, 1997

[51] Int. Cl.⁶ ........................................ A61N 1/05
[52] U.S. Cl. ..................... 607/129; 607/3; 607/5; 601/41
[58] Field of Search .............. 601/41; 607/3–5, 607/10, 119, 129; 600/16, 374

[56] References Cited

U.S. PATENT DOCUMENTS

| | | | |
|---|---|---|---|
| 4,270,549 | 6/1981 | Heilman | 607/129 |
| 4,317,458 | 3/1982 | Yokoyama | 607/122 |
| 5,466,221 | 11/1995 | Zadini et al. | 604/96 |
| 5,484,391 | 1/1996 | Buckman, Jr. et al. | 601/41 |
| 5,593,428 | 1/1997 | Jamshidi | 607/4 |

FOREIGN PATENT DOCUMENTS

94/03228  2/1994  WIPO ...................... 601/41

*Primary Examiner*—William G. Kamm
*Assistant Examiner*—George R. Evanisko
*Attorney, Agent, or Firm*—Townsend and Townsend and Crew LLP

[57] ABSTRACT

An apparatus and method for Cardiac Resuscitation of an arrested heart, for Percutaneous Internal Direct Epicardial Defibrillation, Cardioversion and Pacing with electrodes placeable directly into the chest cavity onto the epicardium via a device entering the chest in a specific area of the anterior chest wall via blunt dissection rapidly creating a passage of negligible size in the chest wall for the introduction of the electrodes, without the need for thoracotomy or for sternotomy and without requiring the use of sharp surgical instruments and without causing pneumothorax. Due to its rapidity of implementation, its safety and simplicity of application, the device can be used by Paramedics in the field at the scene of a cardiac arrest, where the resuscitation efforts are more likely to succeed, for internal direct epicardial defibrillation, cardioversion and pacing.

4 Claims, 11 Drawing Sheets

EPICARDIAL PERCUTANEOUS DEVICE FOR ELECTRICAL CARDIAC THERAPY

BACKGROUND OF THE INVENTION

This invention relates to electrical cardiac therapy devices, specifically to emergency defibrillators, cardioverters and pacemakers.

Electrical therapy is commonly used in cardiac therapy, especially in cardiac resuscitation. Defibrillation, cardioversion and pacemaker therapy play a major role in cardiac resuscitation. Defibrillators and cardiac pacemakers are indeed common devices in the emergency armamentarium. Electrical therapy has proved over the last two decades to be often lifesaving in cardiac arrest settings. Cardiac arrest can result from a variety of cardiac arrhythmias all amenable to electrical therapy. These arrhythmias include ventricular fibrillation, ventricular tachycardia, ventricular asystole and high degree heart blocks.

A defibrillator is a device that administers a controlled electrical shock to patients to terminate a cardiac arrhythmia. The technique of administering the electrical shock is usually referred to as defibrillation if it used to terminate Ventricular Fibrillation or pulseless Ventricular tachycardia. The technique is referred to as Cardioversion if it is administered for other cardiac arrhythmias, typically atrial fibrillation, atrial flutter, or ventricular tachycardia. Typically, in defibrillation the electrical shock is unsynchronized with the cardiac cycle while in cardioversion the electrical shock is delivered in synchronization with the cardiac cycle, at a specific electrical stage of the cardiac cycle.

The defibrillator basically consists of a charging circuit that gradually builds electrical energy to a preset level on a storage circuit. The storage electrical energy is then delivered to the patient through a discharge circuit. The electrical stored energy is delivered via conductive paddles applied to the chest or back of a patient in the External Defibrillator. Another type of Defibrillator is the Automatic Implantable Cardioverter-Defibrillator which consists of a pulse generator with both sensing and shocking electrodes. In the Automatic Implantable Defibrillator the shocking electrodes are usually two epicardial patches placed in anteroposterior position over the heart surface or one epicardial patch and another electrode, the so called transvenous spring electrode, placed in the right ventricular apex, all implanted by thoracotomy or sternotomy i.e. by surgical opening of the chest. Rarely is direct epicardial defibrillation implemented i.e. defibrillation with two epicardial paddles applied directly over the heart in anteroposterior position. Instances of application are traumatic cardiac arrest, open chest surgery or medical cardiac arrest during open chest cardiac massage.

The energy required for Direct or Internal Defibrillation of the heart in these cases is by far less than the energy required with External Defibrillation. Due to the fact that the paddles are directly applied over the heart, the impedance, i.e. the resistance to current flow, is greatly reduced in respect to the commonly used External Defibrillators. There are indications that Direct or Internal Defibrillation is more effective than External Defibrillation. Unfortunately due to the fact that Direct or Internal Defibrillation can be carried out only in patients victim of cardiac arrest via thoracotomy, its applications are severely limited and, practically, it can be carried out only in cases of traumatic cardiac arrest or in patients whose heart arrested during cardiac surgery in the operating room.

Pacemakers are medical devices that deliver an electrical stimulus through electrodes to the heart causing electrical depolarization and subsequent cardiac contraction. Emergency cardiac pacing is required in patients whose primary problem is cardiac impulse formation and br conduction such as hemodynamically compromising unstable bradycardia, high degree of heart block, bradysistolic cardiac arrest and also refractory tachycardias.

Emergency Temporary Cardiac Pacemakers are named according to the location of the electrodes and the pathway the electrical stimulus travels to the heart. They are named Transcutaneous when the electrodes are placed on the skin of the anterior chest wall and the back of a patient, Transvenous when the electrode tip is positioned in the right ventricle or right atrium or both, Transthoracic when the electrodes are placed through the anterior chest wall into the myocardium, i.e. the heart muscle, Epicardial when the electrodes are placed on the surface of the heart, and Transesophageal when the electrodes are positioned within the esophagus.

As in Internal Defibrillation, Epicardial pacing is almost exclusively carried out during open chest surgery for resuscitation of patients with penetrating chest trauma. There are studies documenting the dramatically superior efficacy of epicardial pacing versus the transcutaneous pacing. However, despite dramatic improvement following epicardial pacing, its application is restricted to only a handful of patients due to the obligate requirement of opening surgically the chest for placing the pacing electrodes onto the heart surface.

No epicardial electrical therapy device, Defibrillator or Cardiac pacer, is known to have the electrodes placed onto the heart surface without the surgical opening of the chest with sharp instruments. Such a procedure, besides being associated with high morbidity and mortality, has the unavoidable drawback of having to be carried out only in operating rooms and rarely in Emergency Departments. Due to the invasiveness character of the procedure, epicardial defibrillation and or pacing is presently carried out only in cases when open chest cardiac massage via thoracotomy is carried out.

SUMMARY OF THE INVENTION

It is an object of the present invention to provide an electric cardiac therapy device for defibrillation, cardioversion and pacing with at least one electrode being placeable directly onto the heart surface via introduction into the chest cavity by blunt dissection of the chest wall without surgically opening the chest. Such electrode placement is carried out safely via blunt dissection in a specific area of the chest wall without causing injuries to the chest wall structures, to the heart or to the other intrathoracic organs, and without causing pneumothorax, i.e. collapsing of the lung. Further, the electrode is placed directly onto the heart surface rapidly and safely at the site of a cardiac emergency situation.

The fundamental and unique feature of gaining access to the chest cavity and to the heart without surgically opening the chest, via blunt dissection and blunt entry into the chest cavity for the purpose of epicardial defibrillation and or pacing is not known in any prior art.

The ability of gaining access to the chest cavity via blunt dissection and blunt entry into the chest cavity is critical in rendering epicardial defibrillation, cardioversion and pacing, a procedure that can be practically implemented in a large number of patients. The procedure can be carried out in patients at the scene of a cardiac arrest, where resuscitative efforts are more likely to succeed.

Buckman and Badellino disclosed in their patents, U.S. Pat. Nos. 5,484,391, 5,571,074, and 5,582,580, a method and apparatus for direct cardiac defibrillation and pacing associated with their disclosed direct manual cardiac compression device. The device of Buckman and Badellino is disclosed to be inserted into the chest cavity onto the heart via opening the chest via surgical means, precisely making an incision in the skin of an intercostal space and surgically separating the intercostal space for the purpose of inserting the device. Although the apparatus and method disclosed by Buckman and Badellino present some advantages over the open chest cardiac massage and over the implementation of epicardial defibrillation and or pacing via thoracotomy, it still has the unavoidable drawback of having to be carried out by way of a surgical opening of the chest with a surgical knife with all the complications associated with the surgical opening of the chest and with the unavoidable disadvantage of having to be implemented only in a hospital setting, and not at the scene of a cardiac arrest where resuscitative efforts are more likely to succeed.

It is an object of the present invention to provide an epicardial device for electrical cardiac therapy that can be used in association with all the cardiac resuscitation devices for percutaneous direct cardiac massage disclosed by Zadini et al. in their issued U.S. Pat. Nos. 5,683,364, and 5,466,221, and in their copending U.S. patent application Ser. No. 08/555,985, filed on Nov. 13, 1995, and now pending. All the above references have the very important common feature of placing an expandable member into the chest cavity in front of the heart for the purpose of compressing and decompressing the heart via blunt dissection through the chest wall and blunt entry into the chest cavity. No other known resuscitation device or methods of cardiac resuscitation has the feature of placing the cardiac compression-decompression member for direct cardiac massage into the chest cavity by blunt dissection of the chest wall and blunt entry into the chest cavity.

No other cardiac resuscitation device is known to have the feature of being operated safely, effectively, and swiftly at the scene of the cardiac arrest where the chances of survival are greater.

The combination of the epicardial percutaneous device for electrical cardiac therapy with the cardiac resuscitation device for percutaneous direct cardiac massage makes epicardial defibrillation, cardioversion or pacing a practical procedure usable in conjunction and concurrently with direct cardiac massage as the arrested heart may respond to either electrical therapy or direct cardiac compression-decompression.

Due to its ability of being implemented with minimal invasiveness and safely without damaging intrathoracic organs including the heart owing to the features of gaining access to the chest cavity by blunt dissection and blunt entry, the potentially highly effective emergency procedure of epicardial defibrillation and/or pacing with the present invention can be implemented even at the scene of a cardiac arrest by trained personnel, such as paramedics, at the earliest time when its usefulness is greater.

It is important to point out that gaining access to the chest cavity with a sufficiently small size blunt dissection through the "trigonum sine pleura", which is an area in the inner aspect of the anterior thoracic wall void of lung tissue and of its lining, i.e. pleura, guarantees the unique advantage, in respect of methods of surgically opening the chest, of not causing the complication known as pneumothorax, which is an unavoidable complication when the chest is opened surgically.

The ability of gaining access to the chest cavity via blunt dissection and blunt entry into the chest cavity is critical in offering the significant dual advantage of rendering two potentially highly effective procedures, such as direct heart massage and direct epicardial electrical therapy, concurrently and practically implementable in a large number of patients. Both procedures can be carried out in patients in the field at the scene of a cardiac arrest where resuscitative efforts are more likely to succeed.

DESCRIPTION OF THE PREFERRED EMBODIMENT

Figure 1:
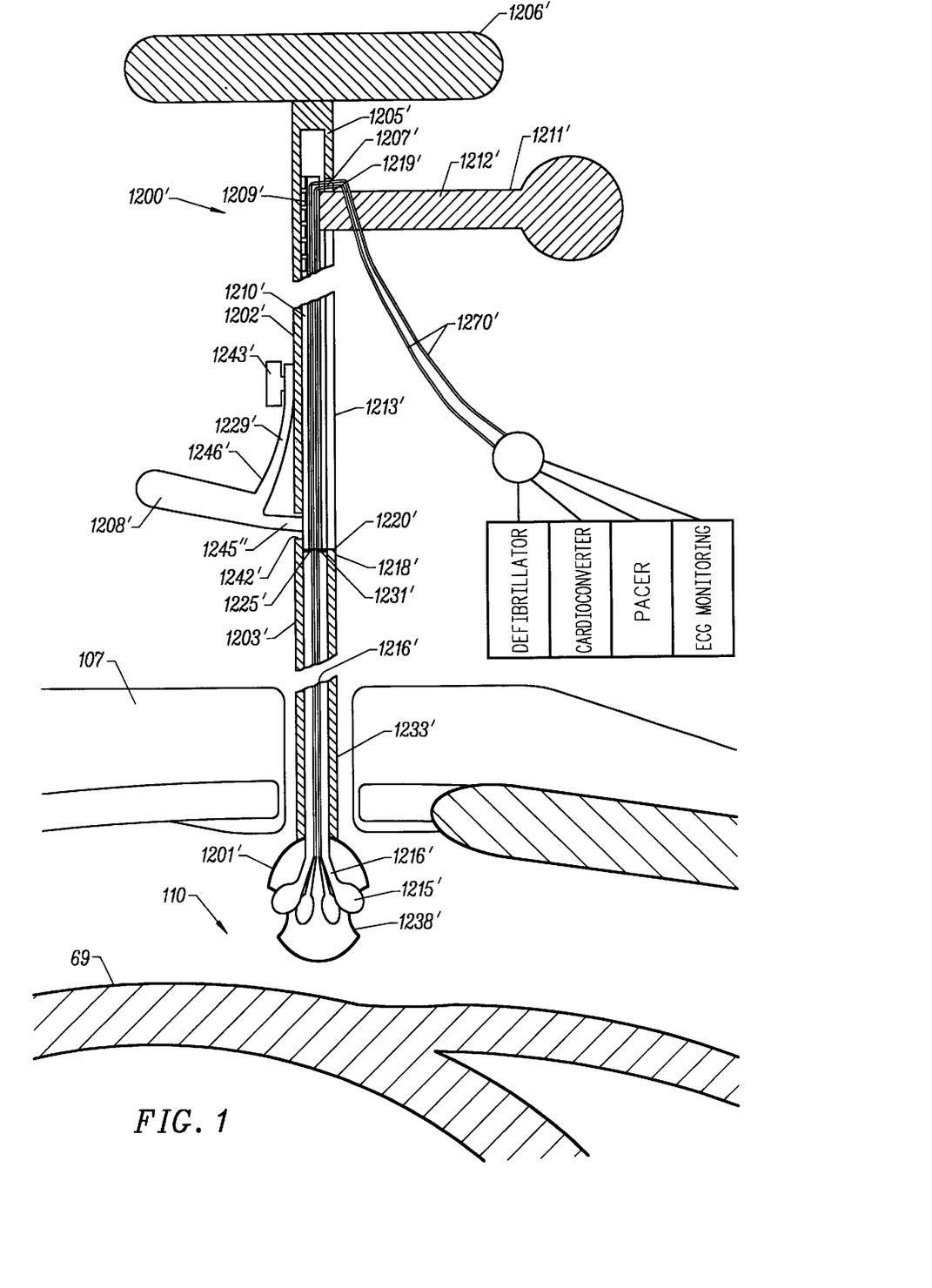
FIG. 1 shows a cross sectional view of an embodiment of the device with its stem tip within the chest cavity prior to deployment of the two electrodes on the epicardium.

An epicardial percutaneous device for electrical cardiac therapy, indicated generally at 1200', is shown in FIG. 1.

The device 1200' is composed of two main components, stem member 1202' and a set of two pairs of diverging electrode-ribs 1216'. Stem member 1202', of general cylindrical hollow shape, comprises hollow stem 1203', distal end or stem tip 1201' and proximal end 1205'. Proximal end 1205' of stem member 1202', is securely connected to handle 1206'. Within hollow stem 1203' is slideably mounted rod 1210'. Rod 1210' is of generally cylindrical shape having an array of notches 1209' on its proximal segment for engagement with locking tab 1246'. Proximal ends 1231' of diverging electrode-ribs 1216' are firmly attached to distal end 1218' of rod 1210'. Hollow stem 1203' is formed with longitudinal slit 1213' for handle arm 1212' of handle 1211'. Longitudinal slit 1213' has proximal end 1219' and distal end 1220'. Locking tab 1246' with flexible arm 1229' is fastened via pin 1243' to hollow stem 1203' and has arrest tooth 1245" engaging opening 1242' in hollow stem 1203'. Tab 1246' has handle 1208' for manual release of locking tab 1246'.

Stem tip 1201' is of general spheroid, elliptical cross section or ovoid shape. The roundness of the stem tip 1201' confers the important feature of bluntness to stem tip 1201' and consents to gain access to the chest cavity by dissecting the chest wall by blunt dissection, which is critical in avoiding injuries to the structures of the chest wall and to the intrathoracic organs, such as the heart. Stem tip 1201' has openings 1238' for passage of electrode-ribs 1216'.

Stem end or tip 1201', firmly attached to distal segment 1233' of hollow stem 1203' of stem member 1202' is of greater width than contiguous distal segment 1233'.

Electrode-ribs 1216' are made of resilient material such as steel or suitable medical grade plastic. If made of steel they require an insulating coat. Also, fiberoptic cables can run with electrode-ribs 1216' within hollow stem 1203', or alternatively electrode-ribs 1216' can be made of suitably resilient fiberoptic material to provide endoscopic visualization of the intrathoracic organs such as the heart and the epicardium for confirmation of proper positioning of pads or webs 1222' on the epicardium. All electrode-ribs 1216' are connected at their respective proximal ends 1225' to distal end 1218' of slideable rod 1210' within hollow stem 1203' of stem member 1202'.

Figure 2:
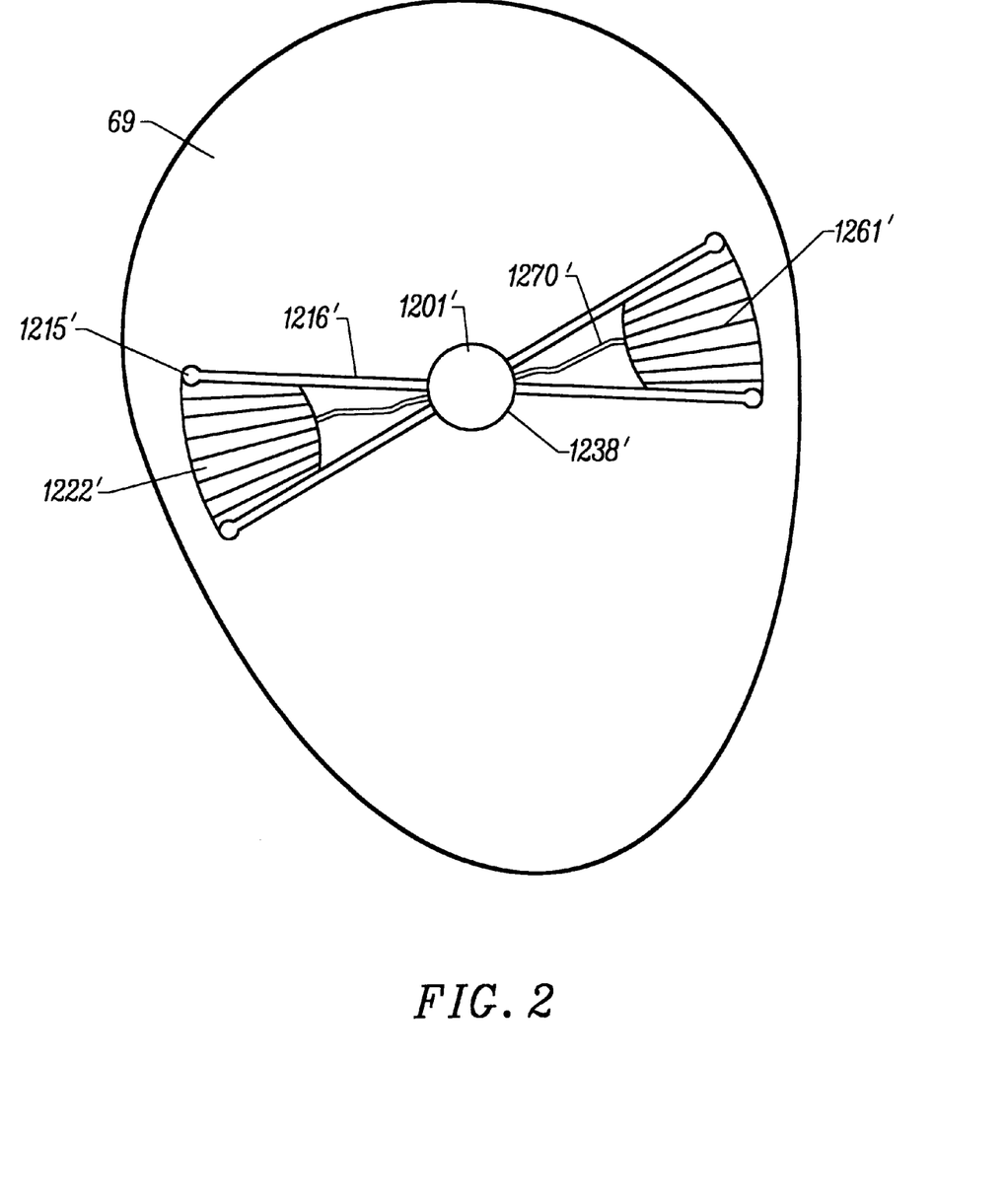
FIG. 2 shows a view of the two deployed electrodes on the epicardium ready for electrical therapy.
Figure 3:
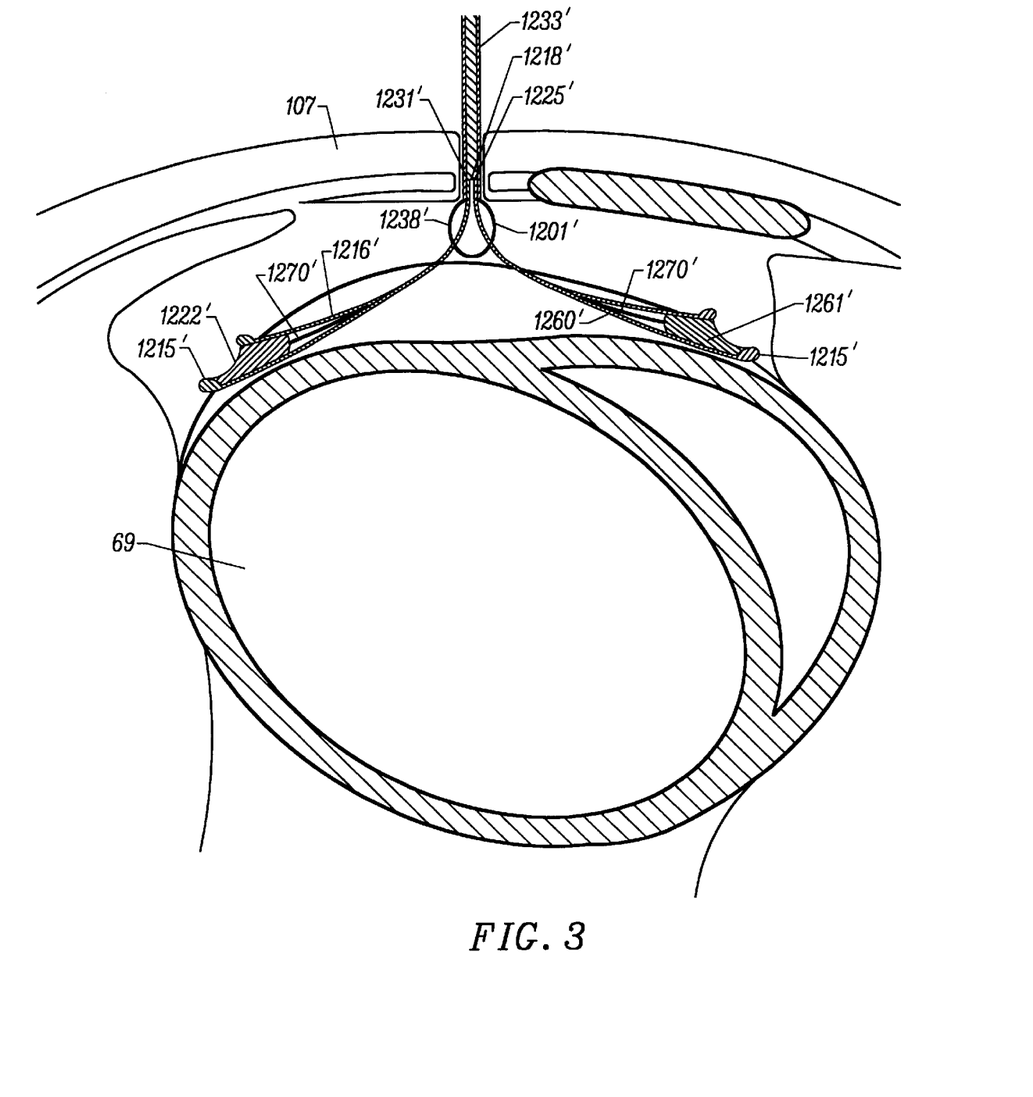
FIG. 3 shows a cross sectional view of the thoracic cavity with the two electrodes deployed and positioned on the epicardium.

As best seen in FIGS. 2 and 3, electrode-ribs 1216' are in a set of two pairs and each rib has distal blunt end 1215'. Each pair of electrode-ribs 1216' has, in correspondence of their distal segment, web 1222' of grossly triangular shape, made of electrical conductive material. As best seen in FIG. 3, web 1222' has an epicardial contacting and conducting surface 1260' and an electrically insulated opposite surface 1261'. Webs 1222' function as electrodes for transmitting electrical current to the heart for defibrillation, cardioversion and pacing, and also function as sensors of cardiac electrical activity and epicardial contact pressure.

An insulated electrically conductive cable 1270' is connected to each web 1222' and is mounted along electrode-ribs 1216' within hollow stem 1203' to exit through opening 1207', formed in hollow stem 1203', to be connected to an external electrical therapy device such as a defibrillator-cardioverter, a cardiac pacing device or to an electrocardiographic monitoring device.

Prior to use, each pair of electrode-ribs 1216' is retained in their entire length within hollow stem 1203' and forced to bunch together very close one to another, against their resiliency which urges them to diverge outwardly one from another in correspondence of their distal segments.

Description of operation of device of FIGS. 1–4.

The operator makes a small superficial incision in the patient's skin on the anterior chest wall, preferably in the left parasternal region along the left parasternal border, in a skin area corresponding to the intrathoracic anatomical area designated as "trigonum sine pleura". Usually such area corresponds to the fourth and fifth intercostal space. However, anatomical variants are possible where the "trigonum sine pleura" extends to contiguous intercostal spaces. Access to the chest cavity can also be gained through the subxyphoideal region.

A skin incision, approximately ⅜" long or less, is carried out on the very superficial layer of the skin, to a depth comprised ordinarily between 1/16" to ⅛" for the purpose of overcoming the resistance of the skin encountered by the blunt tip 1201' of the device in entering the chest wall of a patient. The superficial skin incision is carried out with a suitable surgical instrument such as a lancet or the tip of a surgical knife preferably provided with an arrest to prevent deeper penetration.

Spheroidally shaped tip 1201' of device 1200' is then inserted by the operator into the skin incision. Operator then carefully and gradually advances the device through the chest wall 107 by blunt dissection by holding the device by hand in close proximity of the chest wall 107 and forcing the device downward through the chest wall thickness. By such method the device can only be advanced in steps of predetermined amounts equal to the distance between the chest wall and the hand of the operator holding the device in proximity of the chest wall. In such a fashion the device is advanced through the chest wall in a gradual stepwise manner toward the chest cavity. A number of more sophisticated mechanisms of gradual advancement of the blunt stem tip through the chest wall, achieving a high degree of safety and effectiveness, can be used. Such mechanisms are disclosed by Zadini et al. in their issued U.S. Pat. Nos. 5,683,364, and 5,466,221, and copending U.S. patent application Ser. No. 08/555,589, filed on Nov. 13, 1995, and now pending.

Stem member 1202' is advanced by blunt dissection through the thickness of chest wall 107 until blunt entry opens the passage through the chest wall, i.e. stem tip 1201', is gained into chest cavity 110. Stem tip 1201' of hollow stem 1203' being of a greater width than distal contiguous segment 1233' of hollow stem 1203' allows the operator of the device, upon entry of tip 1201' into the chest cavity 110, to tactually sense entry of the blunt distal stem end 1201' into the chest cavity by the sudden fall of resistance to forward and sideways movement of stem tip 1201', the resistance to forward and sideways movements being present during passage of stem tip 1201' through chest wall 107, due to constraint exerted by chest wall tissues upon stem tip 1201' during its passage through chest wall 107.

A number of more sophisticated mechanisms for sensing entry of the stem tip into the chest cavity, achieving a high degree of safety and effectiveness can be used. Such mechanisms are disclosed by Zadini et al. in their issued U.S. Pat. Nos. 5,683,364, and 5,466,221, and in their copending U.S. patent application Ser. No. 08/555,589, filed on Nov. 13, 1995, and now pending.

When the operator has ascertained penetration of stem tip 1201' of stem member 1202' into chest cavity 110, she or he advances slideable rod 1210' relatively to hollow stem 1203' by holding still with one hand, hollow stem 1203' by its distal segment, and acting upon handle 1211' with his or her other hand so as to move rod 1210' downwardly, toward chest cavity 110. The purpose of holding hollow stem 1203' still and firmly by its distal segment is to avoid accidental advancement of the device towards the heart. Rod handle 1211' is then advanced to place webs 1222' on the proper position on the epicardium. Distal end 1218' of rod 1210' being connected to proximal ends 1225' of electrode-ribs 1216', causes the downward movement of rod 1210' to eject end exit of electrode-ribs 1216' through openings 1238' of stem tip 1201'. Rod 1210' is retained in the chosen position by engagement of arrest tooth 1245" of locking tab 1246' on one of the notches 1209' of rod 1210'. Engaged arrest tooth 1245" of locking tab 1246' will prevent backward and forward displacement of electrode-ribs 1216'. Upon ejection of distal segments of ribs 1216' from stem tip 1201', electrode-ribs 1216' as best seen in FIG. 2, will diverge outwardly one from another as a result of their resiliency.

Webs or pads 1222' of each electrode-ribs 1216' pair will unfold and spread between each pair of electrode-ribs to provide an electrode of conductive surface of suitable size in contact with the heart.

As soon as deployed, webs or pads 1222' are placed in contact with the epicardium by downward resiliency of the ribs and/or by the operator pressing downward on handle 1206' of device 1200'.

The distance between pads 1222' on the epicardium can be suitably adjusted by the operator acting upon handle 1211' to advance or withdraw slideable rod 1210' to the desired position secured by tooth 1245" of tab 1246', which releasably engages notches 1209' of rod 1210'.

The device can also be rotated by the operator around its longitudinal axis in order to position pads 1222' on the desired epicardial areas.

Insulated electrically conductive cable 1270' is connected for use to a defibrillator, a cardioconverter or a pacer to enable percutaneous epicardial defibrillation, cardioversion or pacing. Sensing of cardiac electrical activity is provided by webs or pads 1222'.

Conductive surface 1260' of web 1222' can be provided with accessories such as miniature or micro needles of conductive material arranged in a brush like fashion capable of penetrating through the epicardial lining into the myocardium to provide a type of myocardial electrode for myocardial defibrillation, cardioversion or pacing.

At completion of the electrical resuscitative efforts electrode-ribs 1216' are withdrawn by withdrawing handle 1211' of rod 1210', after manual release of locking tab 1246' by action on handle 1208' to disengage tooth 1245" from notches 1209' of rod 1210'.

Figure 4:
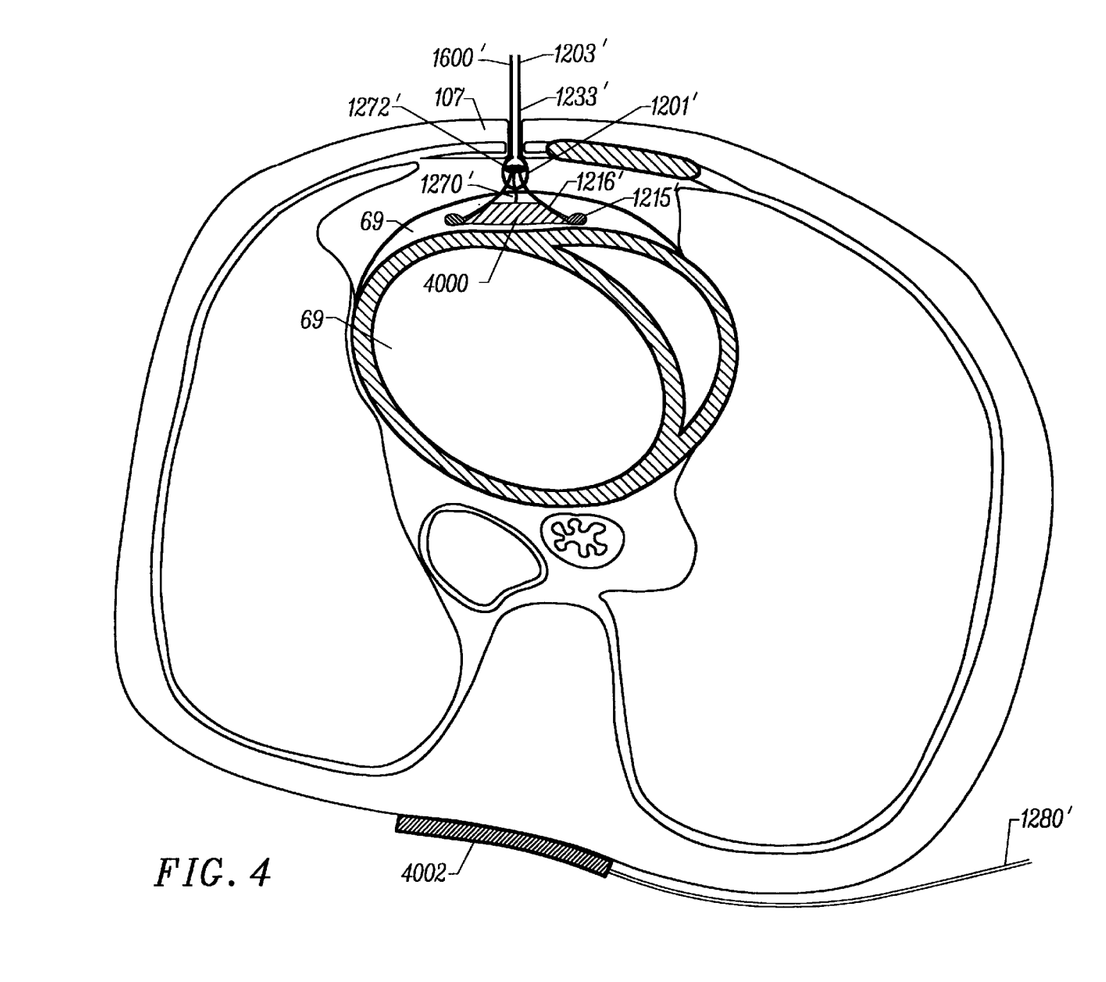
FIG. 4 shows a cross sectional view of the thoracic cavity with an alternative form of the device of FIGS. 1–3 with its single epicardial electrode and its other electrode applied on the skin of the back of the patient.

FIG. 4 shows an alternative form, generally indicated at 1600', of device 1200' of FIGS. 1–3. Structurally, alternative form 1600' differs from device 1200' in having only one pair of electrode-ribs which carries only one epicardial pad/sensor 4000. The single pad/sensor 4000 is positioned on the epicardium, while another pad/sensor 4002 is positioned on the skin of the back of the patient. Stem tip 1201' has opening 1272' to allow exit of electrode-ribs pair 1216'. Access to chest cavity is gained precisely in the same way as with device 1200' of FIGS. 1–3. Insulated electrically conductive cable 1270' connected to epicardial pad 4000 as well as insulated electrically conductive cable 1280' connected to external pad 4002 on the skin of the back of the patient, are connected for use to a defibrillator, a cardioconverter or a pacer to enable percutaneous epicardial defibrillation, cardioversion or pacing. Sensing of cardiac electrical activity can be provided by pads 4000 and 4002.

In FIGS. 5–9 is shown an alternative form, generally indicated at 1070, of device 1200', of FIGS. 1–3, in which the defibrillating, pacing/sensing electrodes are applied to the expandable member of a cardiac resuscitation device for percutaneous direct cardiac massage.

Such percutaneous direct cardiac massager is disclosed by Zadini et al. in their issued U.S. Pat. Nos. 5,683,364, and 5,466,221, and in their copending U.S. patent application Ser. No. 08/555,589, filed on Nov. 13, 1995, and now pending.

Figure 5:
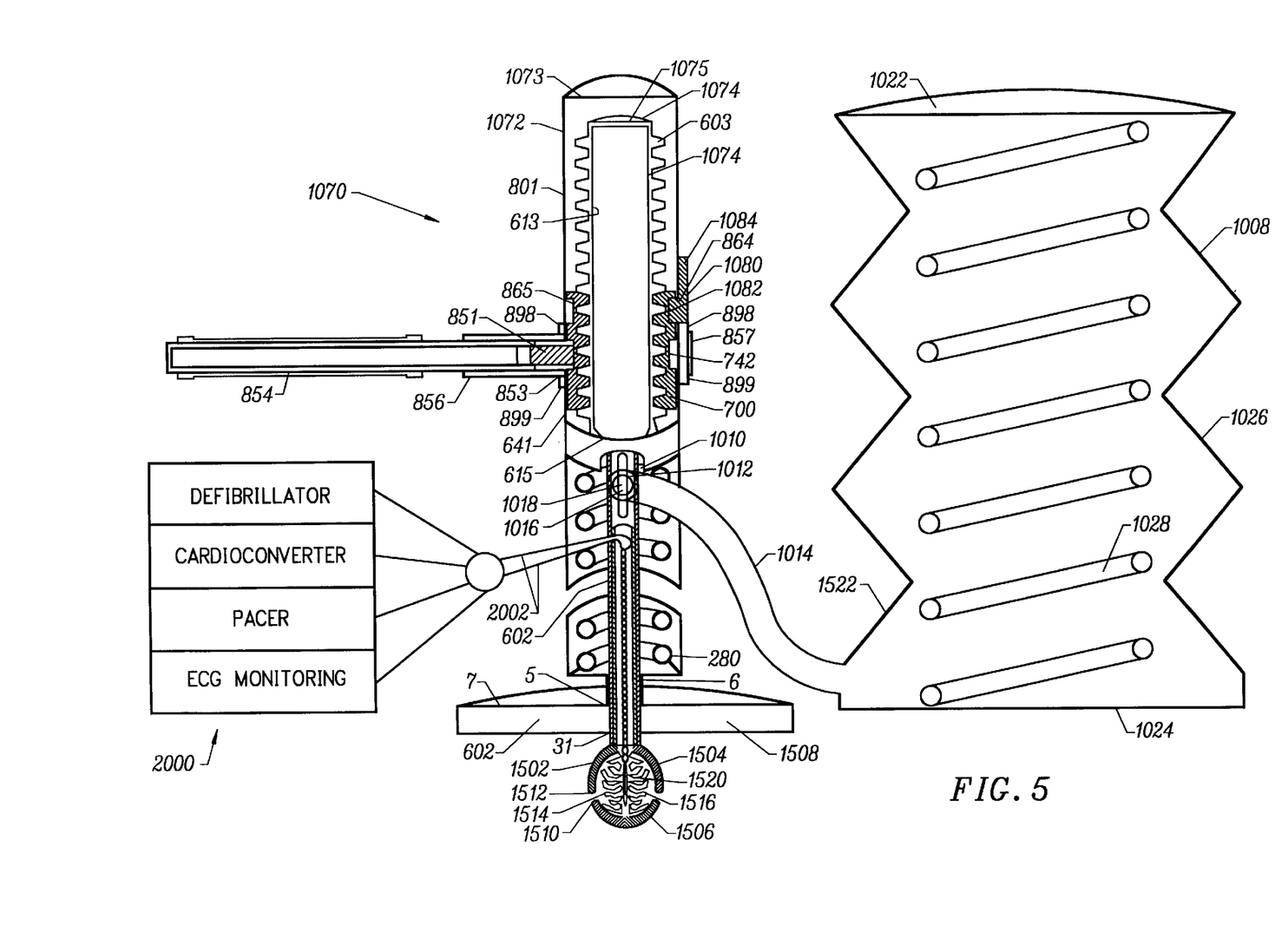
FIG. 5 shows a cross sectional view of an alternative form of the electrical therapy device of FIGS. 1–4 in combination with a percutaneous direct cardiac massager at rest, ready to be used.

Device 1070, as shown in FIG. 5, is composed of five main components: a support case or member generally indicated at 1072, a stem member or unit generally indicated at 1074, an intermediate member generally indicated at 700, an inflating-deflating device generally indicated at 1008 and an epicardial unit for electrical cardiac therapy generally indicated at 2000.

As best shown in FIG. 5, the support case 1072 is hollow and is of a generally tubular, cylindrical shape having a top wall 1073, a body 801 and a distal end 5, including a narrow neck 6 and a flat, circular base 7. The base 7 is preferably formed of transparent material to enable the operator to better visualize the actual position of stem tip or end 1502 of device 1070 on the anterior chest wall of the patient. Also, base 7 is formed with a central opening 31 to allow passage therethrough of stem 602 of the stem member 1074.

The support case 1072 has a generally hollow cylindrical body 801 encircling the intermediate member 700 and the stem member 1074.

Figures 6, 7:
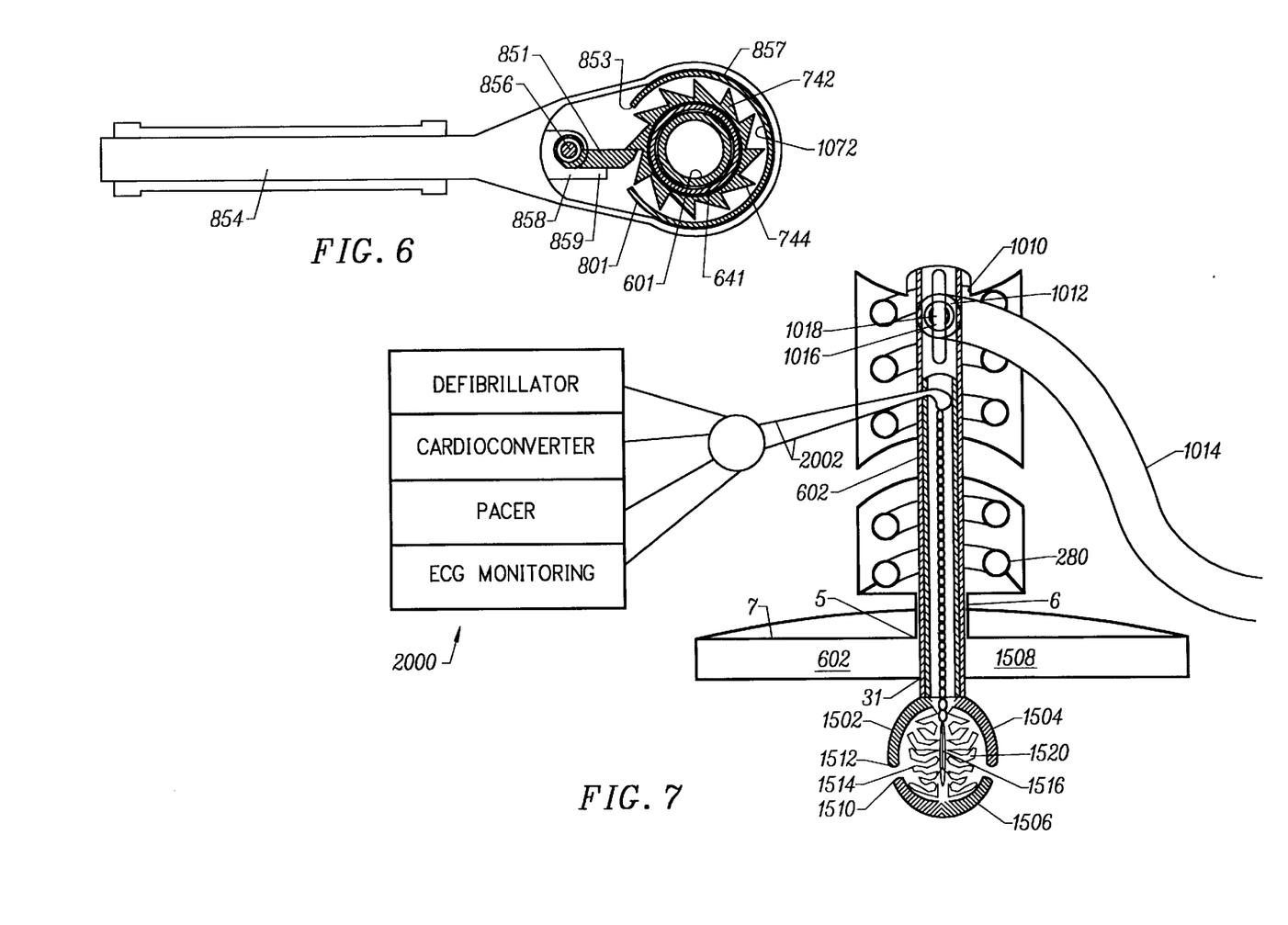
FIG. 6 shows a cross sectional view of a detail of the device of FIG. 5.
FIG. 7 shows a cross sectional view of another detail of the device of FIG. 5.

As better shown in FIGS. 5 and 6, lever 854 encircles with its expanded head 857 support member 1072 at its midportion and is held in that midportion by the presence of two annular rails 898 and 899. Lever 854 carries a dog support 858 to which a dog 851 is pivotally secured via a pin 856 and is provided with dog arrest 859 for dog 851. Dog 851 projects through opening 853 of support member 1072 and reaches for ratcheting engagement teeth 744 of annular rack 742 mounted on the intermediate member 700.

As shown in FIG. 5, tab 1080 is mounted on the outer surface of support member 1072 and is composed of pin 1082 and flexible arm 1084. Pin 1082 of tab 1080 is secured to support case 1072 and engages through opening 864 of annular recess 865.

The intermediate member 700 is interposed between the stem member 1074 and the support case 1072 and is of generally cylindrical shape, with the female threaded portion 641 located approximately midway of the length of support member 1072, and has an annular rack 742 extending about the exterior of the middle of the intermediate member 700, provided with a plurality of outwardly projecting teeth 744.

Stem member 1074 has a generally hollow cylindrical shape and comprises body 613 and hollow stem 602.

Stem member 1074 is closed at its proximal end by top wall 1075. Body 613 of stem member 1074 is provided with a male threaded portion 603 which mates with the female threaded portion 641 of the intermediate member 700. Hollow stem 602 communicates with lower end 615 of body 613 and projects through the base 7 of the support case 1072 to communicate with stem tip 1502.

Spring or resilient member 280 is located within the lower segment of support case 1072, encircles hollow stem 602 and bears against lower end 615 of support member 1074 to urge stem member 1074 upward.

Distal end 1012 of hose 1014 of inflating-deflating device 1008 passes through longitudinal slit 1010 of support case 1072 and is connected to stem 602 at window 1016.

Longitudinal slit 1010 formed on wall of support case 1072 permits that the insertion of distal end 1012 of hose 1014 into stem 602 is maintained in use upon sliding of stem 602 in respect of support case 1072.

Valve 1018 located at connection between distal end 1012 of hose 1014 and stem 602 is shut off in three ways.

Inflating-deflating device 1008 is generally cylindrical in shape with top wall 1022, bottom wall 1024 and lateral pleated walls 1026. Resilient member or spring 1028 is contained within device 1008 to maintain lateral wall 1026 distended in its resting position prior to use. Manually operated inflating-deflating device 1008 may be substituted by a power operated inflating-deflating device.

As best seen in FIG. 7, stem tip 1502 is composed of two parts: proximal part 1504 shaped as an inverted cup firmly attached to the distal end of stem 602 of stem member 1074, and distal part or convex apex 1506. Convex apex 1506 is firmly attached to inner hollow stem 1508 which is telescopically slideable in airtight fashion within hollow stem 602 and has proximal opening 1522. Convex apex 1506 has circular edge 1510 adapted to fit together with circular edge 1512 of circular opening 1514 of proximal part 1504 of stem tip 1502 to form together a spheroidally shaped stem tip 1502. Inner hollow stem 1508 has at least one distal opening 1516 within stem end 1502 in flow communication with expandable member or balloon 1520 which is partially or fully contained in a contracted status within stem end 1502. Hollow inner stem 1508 also provides lateral stability to expandable member 1520 upon its expansion in operation and also provides device 1070 with structure for direction, and allows the operator to have full control on the direction to be given to the expandable member in respect to the position of the heart during compression-decompression.

Figure 8:
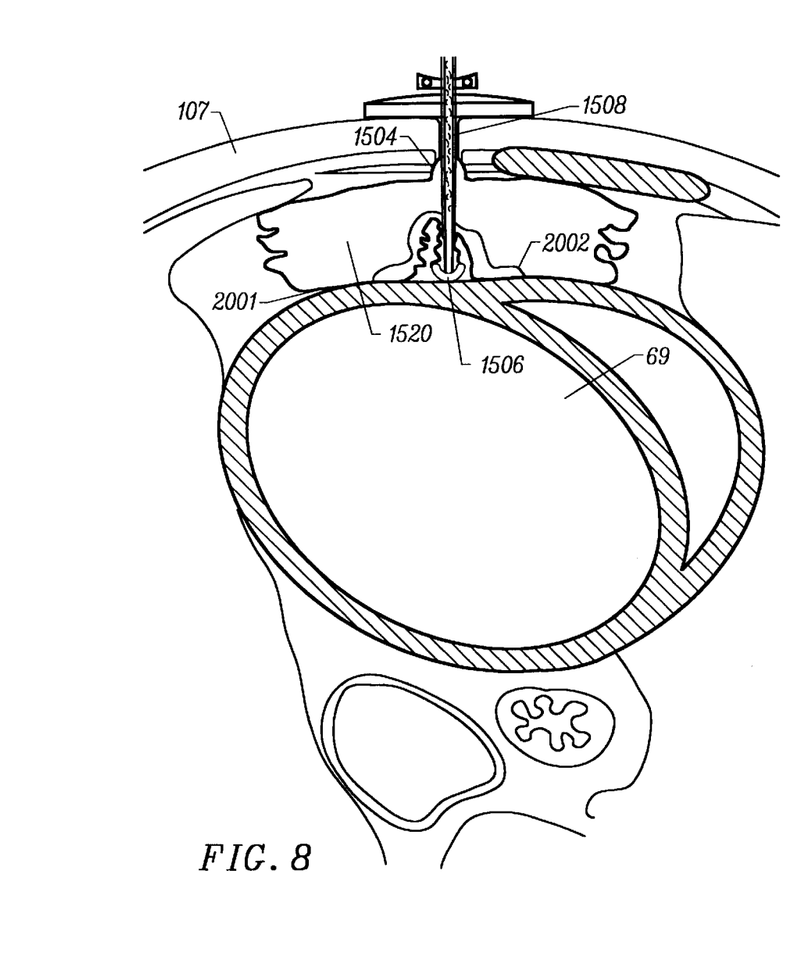
FIG. 8 shows a cross sectional view of a chest of a patient with the device of FIG. 5 in use after penetration of its tip into the chest cavity and at an intermediate inflation stage of the expandable member.
Figure 9:
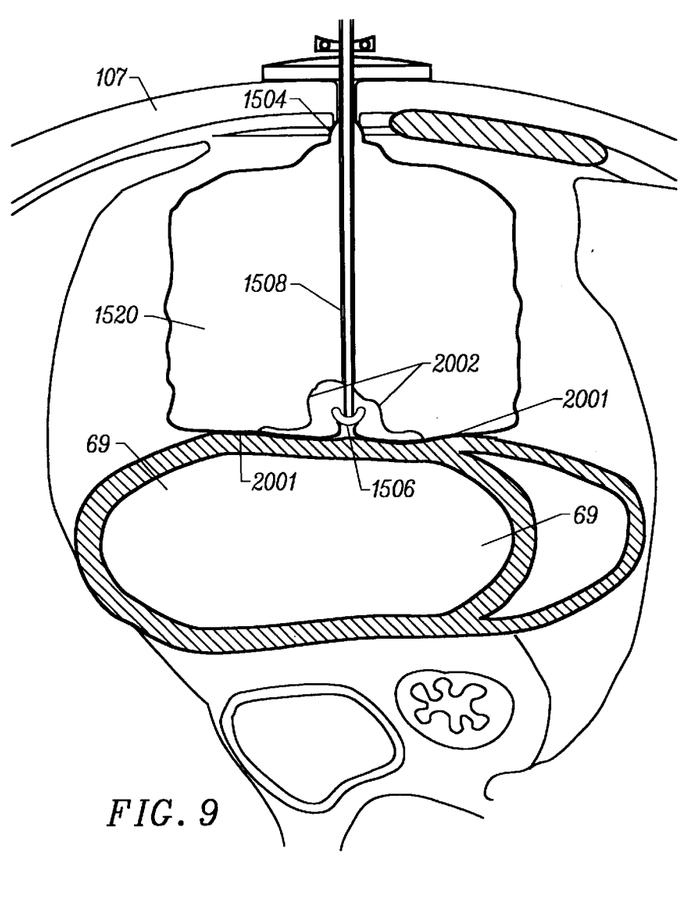
FIG. 9 shows a cross sectional view of a chest of a patient with the expandable member of the device of FIG. 5 fully expanded.

As best seen in FIGS. 8–9, stem member 1074 is provided with two electrode-pads or patches 2001 mounted on the heart contacting surface of expandable member 1520. The two pads 2001 are pliable to allow folding within stem end 1502 and/or in distal segment of hollow stem member 1508 together with balloon 1520 and to be deployed upon expansion of balloon 1520. Each pad 2001 is connected via coiled cable 2002 within stems 1508 and stem 602 to air-sealingly exit through stem 602 and then through the wall of support case 1072 to be connected to an electrical therapy device such as a defibrillator/cardioconverter, to a pacer or to an electrocardiographic monitoring device.

As best shown in FIG. 5, cables 2002 are conveniently coiled within hollow stem 602 to not oppose, by uncoiling, the sliding occurring during use of inner hollow stem 1508 within hollow stem 602.

A fiberoptic cable can be inserted into hollow stems 602 and 1508 to reach transparently made convex apex 1506 of stem tip 1502 to provide visualization of chest cavity organ and confirm proper positioning of the device tip 1502. As the connecting cable 2002, the fiberoptic cable can exit stem 602 in an air-sealingly fashion to be connected to an optical monitoring device. The fiberoptic cable can be withdrawn once the proper position of the tip 1502 has been ascertained to allow free passage of air or gas for the inflation-deflation of balloon 1520. Hollow stem 602, with its extension 1508, can also be used as a pathway for the administration of medication directly to the heart.

Description of operation of device of FIGS. 5–9.

After a small superficial incision is made on the anterior chest wall, which could be as small as one centimeter in length so that blunt end or spheroidally shaped stem tip 1502 wins the skin resistance, in the left parasternal region in a location of the skin corresponding to the intrathoracic anatomical area designated as "trigonum sine pleura", blunt tip 1502 of the device is engaged into the skin incision and is advanced by blunt dissection through the thickness of the chest wall by the operator.

The operator ratchets the lever 854 laterally, while base 7 of the support case 1072 is pressing steadily against the patient's chest. This action causes dog 851 to drive the teeth 744 on rack 742 to rotate the intermediate member 700. Since the operator is preventing rotation of the stem member 1074, and since intermediate member 700 is prevented from advancing by pin 1082 projecting through opening 864 and engaging annular recess 865 of intermediate member 700, the rotation of intermediate member 700 will cause threads 641 to interact with threads 603 of the stem member 1074 to force stem member 1074 to advance stem tip 1502 through the chest wall structure 107 until stem tip 1502 penetrates chest cavity 110. The gradual and slowly controlled advancement of stem 1074 will result in penetration of stem tip 1502 into chest cavity 110. Once the passage of relatively broad stem end 1502 is completed, and relatively narrow stem 602 is engaged in the chest wall hole formed by stem end 1502, the operator will immediately tactually sense entry of blunt stem tip 1502 into chest cavity 110 by the sudden fall of resistance to forward and sideways movements, the resistance to forward and sideways movements being present during passage of stem tip 1502 through chest wall 107, due to constraint exerted by chest wall tissues upon stem tip 1502 during its passage through chest wall 107. Blunt stem tip 1502 is therefore advanced through the thickness of chest wall 107 by blunt dissection until it enters the chest cavity. Upon receipt of this signal, the operator will cease to actuate the lever 854.

The choice of the "trigonum sine pleura" prevents the insurgence of pneumothorax, which inevitably occurs every time the pleural cavity is entered. With regard to the occurrence of pneumothorax, due to the fact that the "trigonum sine pleura" is a substantially restricted area, the choice of such area is only meaningful if the passage opened through the chest wall is significantly small, as it can be achieved with all the embodiments described in this invention. The width of this area being invariably small, ordinarily in the range of less than two/two and a half centimeter, it is critical that the heart compressing member which has to be passed through the chest wall to enter the chest cavity is contracted to a comparably small size, i.e. less than the width of the "trigonum sine pleura".

Upon entry of blunt stem tip 1502 into the chest cavity, the operator will be alerted of the occurred entry of stem tip 1502. Balloon 1520 will then be inflated by the operator as follows. The operator will open valve 1018, and then compress pneumatic source or inflating-deflating device 1008. Air or suitable gas such as $CO_2$ will flow into hollow inner stem through opening 1522 of inner hollow stem 1508 and will exit through distal opening 1516 located within stem tip 1502 to enter balloon 1520 enabling inflation of balloon 1520. As balloon 1520 begins to inflate, as seen in FIG. 8, hollow inner stem 1508, being telescopically slideable within hollow stem 602, will be dragged forward with convex apex 1506 to which it is firmly attached, convex apex 1506 of stem tip 1502 being firmly attached to the heart contacting surface of balloon 1520.

FIG. 9 shows balloon or expandable member 1520 inflated to the required pressure to achieve cardiac compression.

As shown in FIGS. 8–9, pads 2001 will contact the epicardium as soon as balloon 1520 begins to inflate. Besides providing guidance to the direction of compression and decompression of the heart, telescopically sliding hollow stems 602 and 1508 provide guidance for proper placement of pads 2001 on the epicardium. The device at this point can be used by the operator both for direct compression of the heart and for electrical therapy. With this device both operations can be conveniently carried out simultaneously.

Alternatively, device 1070 can be provided with a single epicardial pad while the other pad is positioned externally on the skin of the back of the patient. The epicardial pad can be either attached to the balloon or to stem tip convex apex 1506.

Figure 10:
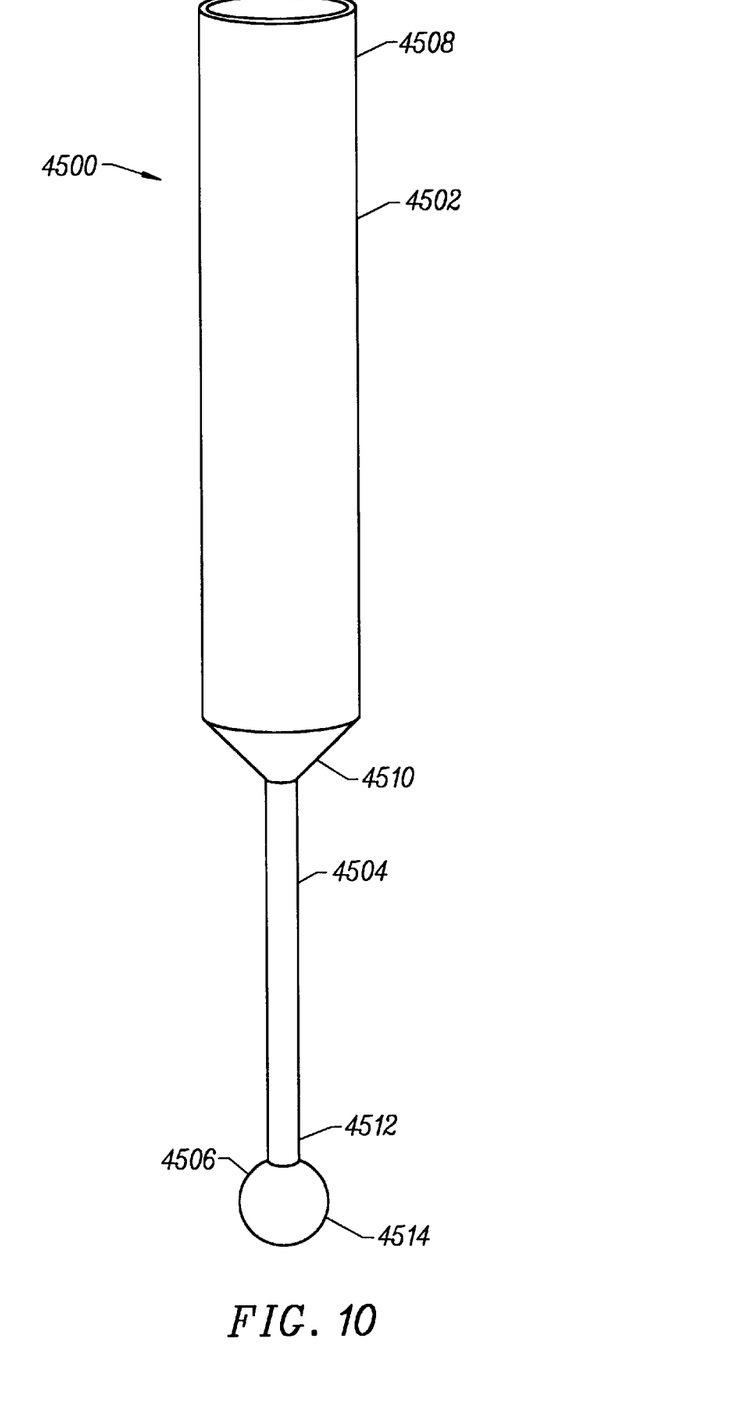
FIG. 10 shows a view of a device for opening a passage through the chest wall and entering the chest cavity by blunt dissection to enable the insertion of the electrodes into the chest cavity onto the epicardium.
Figure 11:
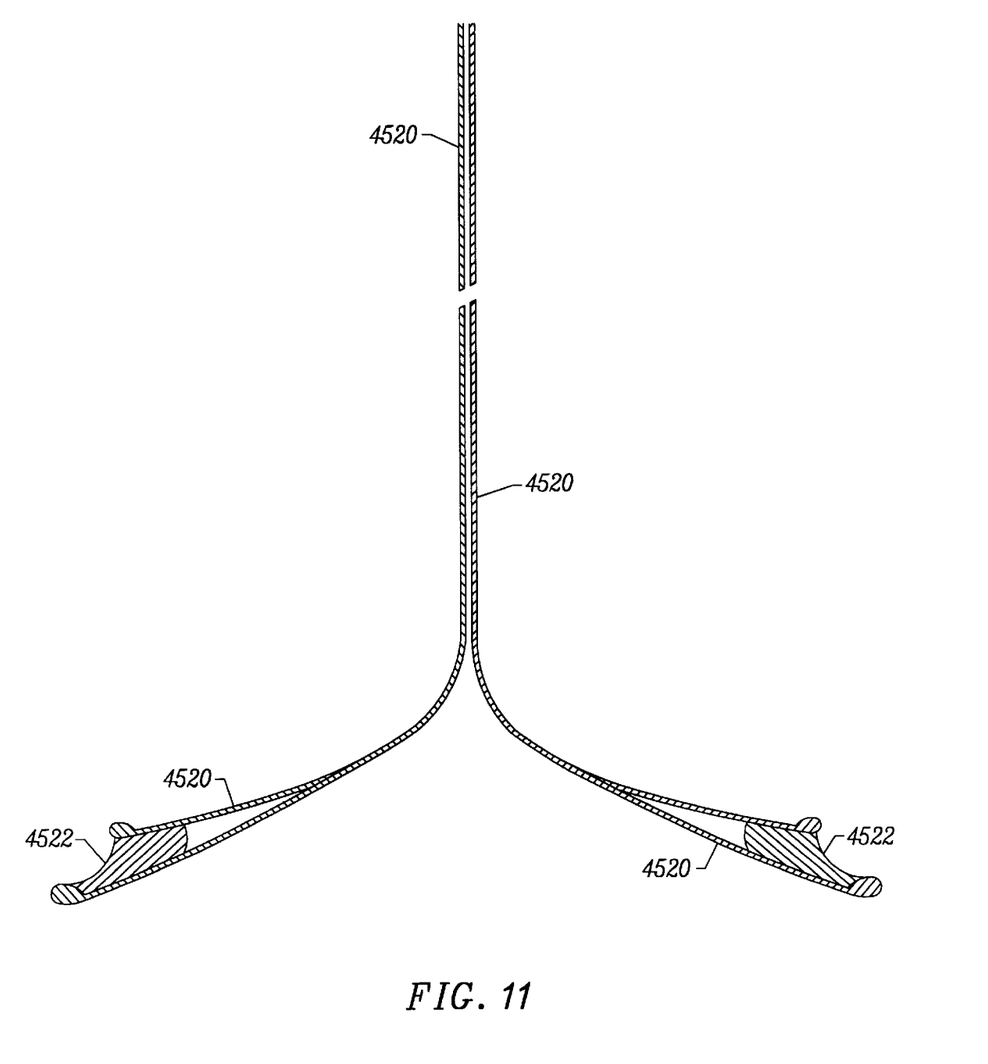
FIG. 11 shows the electrical component of the device of FIG. 10.

FIGS. 10–11 show an alternative form of device 1200' of FIGS. 1–4 in which the structure for opening a passage via blunt dissection through the chest wall are physically separated from the device component used for electrical therapy.

The structure for opening the passage through the chest wall or chest wall blunt dissector, generally indicated at 4500, is composed of handle 4502, stem 4504 and dissecting blunt tip 4506. Handle 4502 is of generally cylindrical hollow shape having proximal end 4508 and distal end 4510 and is firmly connected by distal end 4510 to hollow stem 4504 of smaller diameter than handle 4502. Dissecting blunt tip 4506 of generally spheroidal shape is firmly attached to distal end 4512 of hollow stem 4504. Stem tip 4506 can be provided with opening 4514 in communication with the interior of hollow stem 4504 and handle 4502 for passage of electrode-ribs 4520. Electrode ribs 4520 are similar to electrode ribs 1216' of FIGS. 1–4 in design and operation.

Chest wall blunt dissector 4500 is operated precisely as device 1200' of FIGS. 1–4 up to the point when the operator has sensed entry of the blunt tip 4506 into the chest cavity. Upon reaching the chest cavity by blunt dissection with chest wall blunt dissector 4500, the operator introduces and advances electrode-ribs 4520 into hollow handle 4502 through hollow stem 4504, through openings 4514 of tip 4506 of chest wall blunt dissector 4500, to properly place pads 4522 of electrode-ribs 4520 onto the epicardium ready for use.

Alternatively chest wall blunt dissector 4500 can be withdrawn from the chest, once it has gained access into the chest cavity by creating a hole through the chest wall, to leave a passage for the subsequent step of introducing electrode-ribs 4520.

For this purpose chest wall blunt dissector can be made solid rather than hollow.

Figure 12:
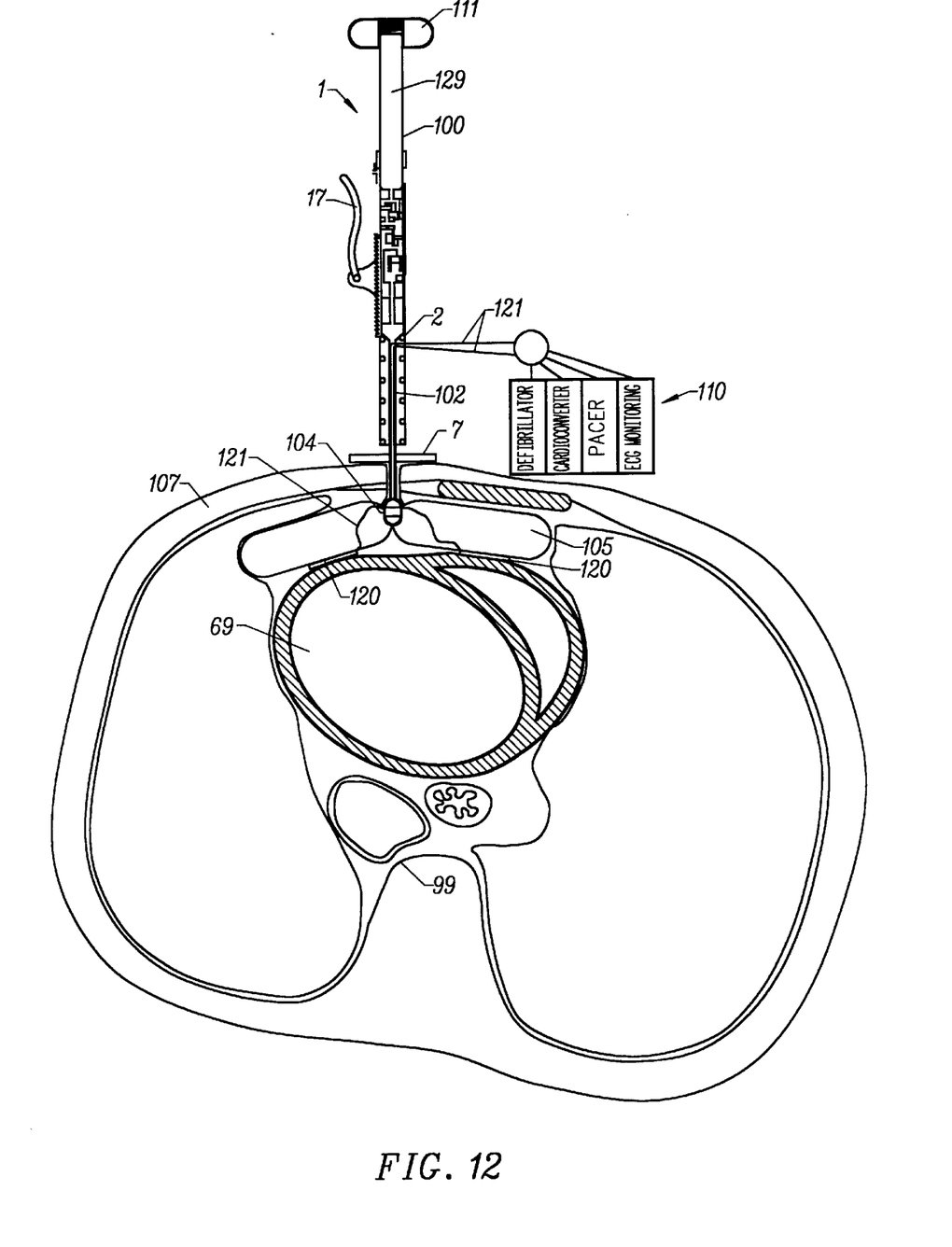
FIG. 12 shows a schematic cross sectional view of an alternative form of the electrical therapy device of FIGS. 1–4 in combination with an alternative form of the percutaneous direct cardiac massager illustrated in FIGS. 5–9 at an initial stage of operation.
Figure 13:
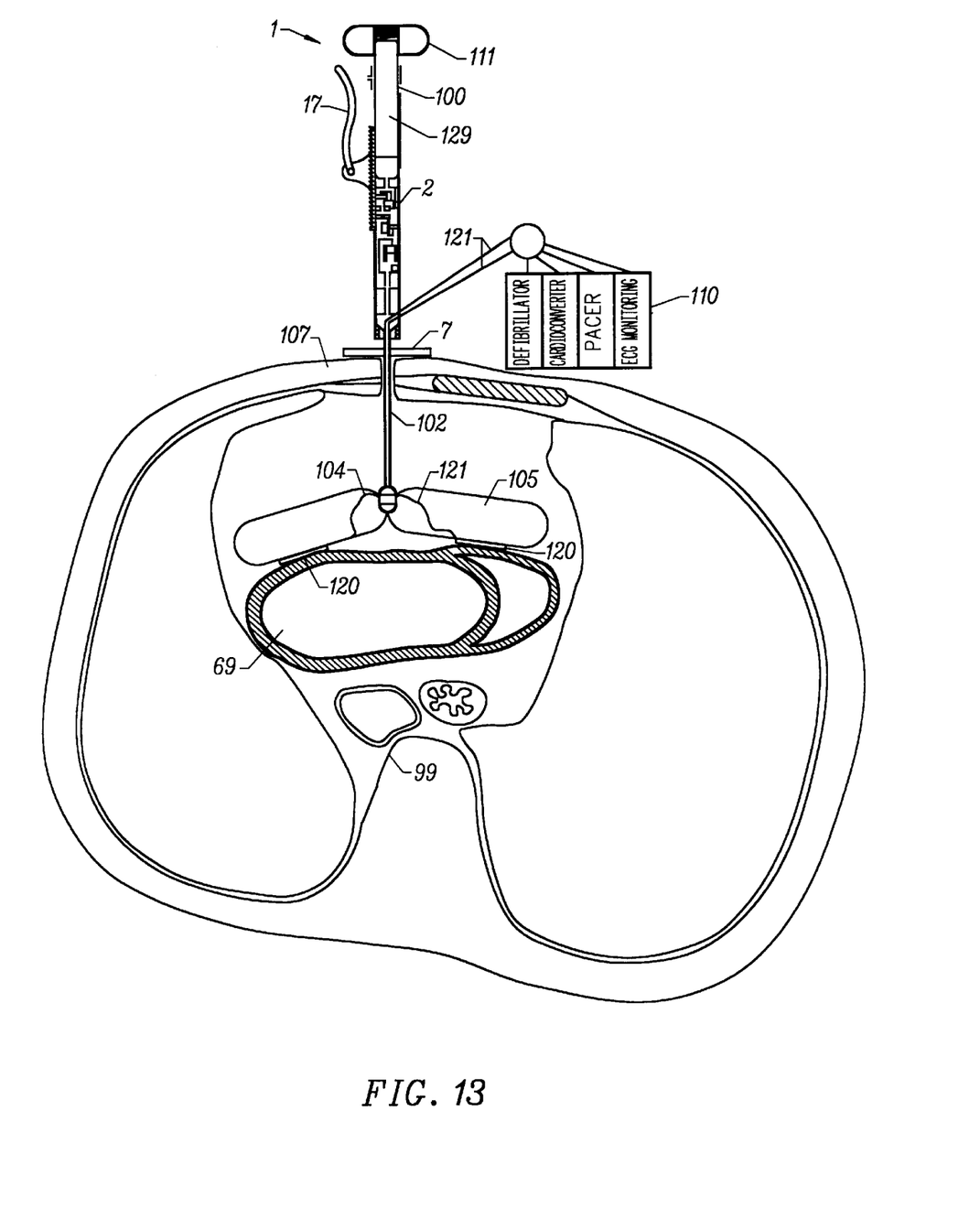
FIG. 13 shows the device of FIG. 12 at a further stage of operation.

FIGS. 12–13 show an alternative form of the Epicardial Percutaneous Device for Electrical Cardiac Therapy of FIGS. 1–4 in combination with an alternative form of the Cardiac Resuscitation Device for Percutaneous Direct Cardiac Massage illustrated in FIGS. 5–9. This type of Cardiac Resuscitation Device for Percutaneous Direct Cardiac Massage has been fully disclosed by Zadini et al. in their issued U.S. Pat. Nos. 5,683,364, and 5,466,221, and in their copending U.S. patent application Ser. No. 08/555,589, filed on Nov. 3, 1995, and now pending. Applicants here disclose the most important features in combination with the Epicardial Percutaneous Device for Electrical Cardiac Therapy. As shown in FIG. 12, the device, generally indicated at 1, is composed of support case 2, of generally cylindrical shape, and stem unit 100 coaxially slideable within support case 2, and electrical unit 110. Stem unit or member 100 has proximally handle 111 for manipulation of the device and distally stem 102 with blunt stem tip or end 104, of general spheroidal shape, which houses, with the device at rest, expandable member or balloon 105. Within stem unit 100 is contained in its proximal segment pneumatic container 129 for inflation of balloon 105. Lever 17 acts upon stem unit 100 to permit gradual controlled advancement of blunt stem tip 104 of stem 102 into the chest cavity through chest wall 107. In use, the operator, after the initial skin incision in the same areas of the anterior chest wall used for all the previously described devices, inserts stem tip or end 104 of device 1 into the incision. He or she then acts upon lever 17 which advances stem tip 104 through the thickness of the chest wall 107. Stem tip 104, during its advancement, creates a passage through the thickness of chest wall 107 via blunt dissection, and enters bluntly and safely due to its blunt features into the chest cavity in front of the heart. At this point, as shown in FIG. 12, balloon or expandable member 105 is automatically inflated to a fully inflated status as shown in FIGS. 12–13 by pneumatic container 129. Unlike device 1070, in which cardiac compression is achieved by alternating inflation and deflation of the balloon, in this alternative form the balloon 105 is fully inflated to a predetermined shape and size and maintained in such expanded status in order to provide a sufficiently rigid heart contacting surface for direct cardiac massage. As shown in FIG. 13, the operator by acting upon handle 111 will press stem unit 100 downward causing compression of the heart and, by releasing the downward pressure on handle 111, will cause decompression and blood refilling of the heart.

Conductive, pliable, foldable or contractible pads 120 of electrical unit 110, connected to a defibrillator, cardioverter or pacer, or to an electrocardiographic monitoring device via cable 121, will contact the epicardium when balloon 105 will begin to inflate. The device at this point can be used by the operator both for direct compression of the heart and for electrical therapy. As in device 1070 of FIGS. 5–9, both operations can be conveniently carried out simultaneously. As in device 1070 of FIGS. 5–9, the device 1 can be provided with fiberoptic means of visualization for ascertaining proper positioning of the electrical pads on the epicardium.

What is claimed is:

1. A cardiac resuscitation device comprising:
   a stem having a rounded tip blunt dissector for bluntly dissecting the chest cavity; and
   at least one electrode on the stem adapted to contact the heart when the rounded tip of the stem is in the chest cavity.

2. The cardiac resuscitation device of claim 1 further comprising:
   a heart compressing member deployable from the stem when the rounded tip is in the chest cavity.

3. A method for cardiac resuscitation comprising the steps of:
   passing a rounded end of a blunt dissector through a chest wall to bluntly dissect a passage into a chest cavity,
   engaging at least one electrode directly on a surface of a heart wherein said electrode is disposed on the blunt dissector, and
   applying electrical pulses to said electrode.

4. The method for cardiac resuscitation of claim 3 further comprising the step of:
   deploying a heart compression member from the blunt dissector for cardiac compression through said passage for direct cardiac compression and decompression.

* * * * *